United States Patent [19]
Jiang et al.

[11] Patent Number: 6,030,350
[45] Date of Patent: Feb. 29, 2000

[54] DEVICE AND METHOD FOR MEASURING PHONATION THRESHOLD PRESSURE

[75] Inventors: Jack Jiang; Timothy G. O'Mara; David G. Hanson, all of Chicago, Ill.

[73] Assignee: Northwestern University, Evanston, Ill.

[21] Appl. No.: 09/124,388

[22] Filed: Jul. 29, 1998

[51] Int. Cl.[7] .............................. A61B 5/103; A61B 5/08; A61F 5/58

[52] U.S. Cl. .......................... 600/587; 600/538; 600/300; 600/23; 600/586

[58] Field of Search .................................. 600/538, 586, 600/300, 587, 590, 23, 24; 73/644

[56] References Cited

U.S. PATENT DOCUMENTS

| | | | |
|---|---|---|---|
| 3,925,616 | 12/1975 | Sondhi ..................................... | 704/201 |
| 4,807,291 | 2/1989 | Hoffmann et al. ....................... | 704/205 |
| 5,377,688 | 1/1995 | Aviv et al. ............................... | 600/560 |
| 5,515,860 | 5/1996 | Aviv et al. ............................... | 600/560 |

OTHER PUBLICATIONS

Koike et al., *Folia Phoniatr.* (Basel), 20: 360–80 (1968).
Lieberman, *J. Acoust. Soc. Am.*, 43:1157–64 (1968).
Lieberman, *J. Acoust. Soc. Am.*, 45:1537–43 (1969).
Löfqvist et al., *J. Acoust. Soc. Am.*, 72(2):63–5 (1982).
Netsell, *Phonetica*, 20:68–73 (1969).
Nishida et al., *Otologica Fukuoka*, 10:264–70 (1964).
Nishida, *Otologica Fukuoka*, 13(Supp. 1):44–66 (1967).
Rothenberg, *J. Speech Hear. Disord.*, 47:219–23 (1982).
Sawashima et al., *Ann. Bull. RILP*, 17:23–32 (1983).
Smitheran et al., *J. Speech Hear. Disord.*, 46:138–46 (1981).
Shipp, *J. Phonetics*, 1:167–170 (1973).
Tanaka et al., *J. Acoust. Soc. Am.*, 73:1316–21 (1983).
Titze, *J. Acoust. Soc. Am.*, 85:901–6 (1989).
Titze et al., *J. Acoust. Soc. Am.*, 97(5):3080–3084 (1995).
Titze, in *Vocal physiology: voice production, mechanisms and functions*, pp. 227–238 (Fugimara ed., Raven Press, 1988).
van den Berg, *Folia Phoniatr.* (Basel), 8:1–14 (1956).
Verdolini–Marston et al., *J. Voice*, 8(1):30–47 (1994).
Verdolini–Marston et al., *J. Voice*, 4(2):142–151 (1990).
Wexler et al., *Annals Oto., Rhin & Laryn.*, 98(9):668–73 (1989).
Akerlund et al., *J. Voice*, 8(3):263–270 (1994).
Bard et al., *Ann. Otol. Rhino. Laryngol.*, 101:578–82 (1992).
Hertegard et al., *J. Voice*, 9:149–55 (1995).
Holmberg et al., *J. Acoust. Soc. Am.*, 84(2):511–529 (1988).
Isshiki, *J. Speech Hear. Res.*, 7:17–29 (1964).
Jiang et al., *Laryngoscope*, 103(8):872–882 (1993).
Kitajima et al., *Acta Otolaryngologica*, 109:473–8 (1990).
Kitajima et al., *Acta Otolaryngologica*, 113:553–9 (1993).
Kitzing et al., *Medical and Biological Eng.*, 13:644–8 (1975).

*Primary Examiner*—Cary O'Connor
*Assistant Examiner*—Navin Natnithithadha
*Attorney, Agent, or Firm*—Sheridan Ross P.C.

[57] ABSTRACT

The invention provides a device and method for measuring phonation threshold pressure. The method and device are useful for diagnosing and evaluating voice disorders and pathologies affecting the vocal tract and for evaluating treatments of such disorders and pathologies.

29 Claims, 5 Drawing Sheets

TRANSGP = SUBGP − SUPRAGP =

DEVICE AND METHOD FOR MEASURING PHONATION THRESHOLD PRESSURE

This work was supported, in part, by grants P60 DC 94-002-02, R01 DC 00254-11 and T32 DC 0015-15 from the National Institutes of Health. The government may have certain rights in the invention.

FIELD OF THE INVENTION

The invention relates to a device and method for measuring phonation threshold pressure. The method and device are useful for diagnosing and evaluating voice disorders and pathologies affecting the vocal tract and for evaluating treatments of such disorders and pathologies.

BACKGROUND

Phonation threshold pressure is defined as the minimum subglottal pressure that is necessary to produce phonation for a given laryngeal configuration. Mathematical models and animal studies have suggested that phonation threshold pressure should increase with pathological phonation (Titze, *J. Acoust. Soc. Amer.*, 85:901–6 (1989); Wexler et al., *Annals Oto, Rhin. & Laryn.*, 98:668–73 (1989)). Phonation threshold pressure can be used as a measure of the ease with which phonation can be produced, and this measure should also be a clinically useful measurement in the evaluation of clinical voice disorders.

Many methods have been described to measure subglottal pressure: (1) directly by tracheal puncture (Isshiki, *J. Speech Hear. Res.*, 7:17–29 (1964)); (2) directly using a miniature pressure transducer inserted through the nose and placed in the throat (Kitzing et al., *Medical and Biological Eng.*, 13:644–8 (1975); Koike et al., *Folia Phoniatr.* (Basel), 20:360–80 (1968)); (3) indirectly using an intra-esophageal balloon (Lieberman P., Direct comparison of subglottal pressure and esophageal pressure during speech (Lieberman, *J. Acoust. Soc. Am.*, 43:1157–64 (1968); Lieberman, *J. Acoust. Soc. Amer.*, 45:1537–43 (1969); van den Berg, *Folia Phoniatr.* (Basel), 8:1–14 (1956)); (4) indirectly by placing a subject in a body plethysmograph (Tanaka et al., *J. Acoust Soc. Amer.*, 73:1316–21 (1983); and (5) indirectly by measuring the intra-oral pressure (Hertegard et al., *J. Voice*, 9:149–55 (1995); Kitajima et al., *Acta Otolaryngologica*, 109:473–8 (1990); Lofqvist et al., *J. Acoust. Soc. Amer.*, 72:63–5 (1982); Netsell, *Phonetica*, 20:68–73 (1969); Rothenberg, *J. Speech Hear. Disord.*, 47:219–23 (1982); Smitheran et al., *J. Speech Hear. Disord.*, 46:138–46 (1981); Kitajima et al., *Acta Otolaryngologica*, 113:553–9 (1993)). However, none of these methods are practical for routine clinical use. Further, direct measurement of subglottal pressure requires an invasive procedure and knowing the subglottal pressure is not, in most cases, sufficiently important for subjects or patients to agree to the risks of these invasive procedures.

One non-invasive technique for the measurement of subglottal pressure is the airflow interruption technique. Pressures measured using this technique have been compared to actual subglottal pressures measured by tracheal puncture in the same subjects, and good correspondence between the measurements has been reported (Nishida et al., *Otologica Fukuoka*, 10:264–70 (1964); Sawashima et al., *Ann. Bull. RILP*, 17:23–32 (1983); Bard et al., *Ann. Otol. Rhino. Laryngol.*, 101:578–82 (1992)). Despite the promise of the airflow interruption technique, it is not yet in clinical use. There have been questions as to the relevance and usefulness of the measurements made with it to date for the diagnosis and evaluation of voice disorders and pathologies affecting the vocal tract.

A simple non-invasive technique for the clinical measurement of phonation threshold pressure would be desirable. One non-invasive technique for the measurement of phonation threshold pressure has been reported which involves the measurement of oral pressure using a translabial catheter. See Verdolini-Marston, et al., *J. Voice*, 4, 142–151 (1990). However, this technique is complex, requiring that subjects be trained for 5–10 minutes, and many test results have to be discarded because satisfactory results could not be obtained. No reports are known of the measurement of phonation threshold pressure using the airflow interruption technique.

SUMMARY OF THE INVENTION

The invention provides a device and method for measuring a phonation threshold pressure in a human. The device comprises:

a housing having a first opening and a second opening;

a member adapted for receiving an airflow from a human's mouth or from a human's mouth and nose and for conveying the airflow into the first opening of the housing, the member comprising a connector adapted for connecting the member to the first opening of the housing;

a valve having at least an open and a closed position, the valve being positioned with respect to the first and second openings of the housing so that the valve can completely obstruct air flow through the housing when it is in the closed position, the valve being connected to a valve controller, the valve controller being connected to a valve switch which can generate an electrical signal, the valve controller being adapted to open and close the valve in response to the signal from the valve switch;

a microphone positioned in the housing so as to be able to detect the level of sound in the housing, the microphone being capable of generating an electrical signal in response to the level of sound detected by the microphone, the microphone being connected to an acoustic signal amplifier which amplifies the electrical signal generated by the microphone; and a pressure sensor connected to the housing so as to be able to detect the level of pressure between the first opening of the housing and the valve, the pressure sensor being capable of generating an electrical signal in response to the level of pressure detected by the pressure sensor, the pressure sensor being connected to a pressure signal amplifier which amplifies the electrical signal generated by the pressure sensor;

the valve switch, acoustic signal amplifier, and pressure signal amplifier being connected to a data acquisition and processing unit that receives and processes the signals from the valve switch and the two amplifiers to provide at least the sound levels and pressures necessary for the calculation of the phonation threshold pressure.

The method of the invention for determining a phonation threshold pressure in a human comprises having the human make and sustain a phonation at one or more selected acoustic levels, thereby producing an airflow which is conveyed into the housing of the device of the invention. Then, the valve switch of the device is switched so as to cause the valve controller to close the valve of the device, thereby obstructing the airflow through the housing of the device. The signals from the valve switch and the amplifiers of the device are acquired for a period of time from at least the time of the switching of the valve switch until the pressure in the housing reaches a maximum. These signals are processed to calculate the phonation threshold pressure.

Finally, the invention provides a method of diagnosing or evaluating a voice disorder or a pathology affecting the vocal tract in a human patient. The method comprises determining the phonation threshold pressure of the patient using a device that briefly obstructs an airflow produced by the patient during phonation and comparing the phonation threshold pressure of the patient with the phonation threshold pressures of humans not suffering from a voice disorder or a pathology affecting the vocal tract, the phonation threshold pressures being determined in the same manner as for the patient.

BRIEF DESCRIPTION OF THE DRAWINGS

In FIG. 3A, the actual subglottal pressure measured through the tracheostomy tube of the patient is also shown.

DETAILED DESCRIPTION OF THE PRESENTLY PREFERRED EMBODIMENTS OF THE INVENTION

When the vocal tract is obstructed above the glottis during sustained phonation, a pressure peak is generated in the vocal tract which represents expiratory lung pressure. This expiratory lung pressure will be equal to the subglottal pressure, and subglottal pressure can be estimated with reasonable accuracy from the expiratory lung pressure using a brief interruption of airflow (the airflow interruption technique). See Sawashima et al., *Ann. Bull. RILP,* 17:23–32 (1983); Bard et al., *Ann. Otol. Rhino. Laryngol.,* 101:578–82 (1992); and Nishida et al., *Otologica Fukuoka,* 10:264–70 (1964).

In normal phonation the subglottal pressure can be considered as the sum of the phonation threshold pressure and a driving pressure. When subglottal pressure is less than phonation threshold pressure, phonation does not occur. Phonation occurs only when the subglottal pressure is equal to, or greater than, phonation threshold pressure. Under physiological conditions, supraglottal pressure is equal to atmospheric pressure, and transglottal pressure represents the difference between the subglottal pressure and supraglottal pressure. Therefore, the phonation threshold pressure, the minimum subglottal pressure that is necessary to sustain phonation, is also equal to the minimum transglottal pressure under ordinary conditions.

Figure 1A:
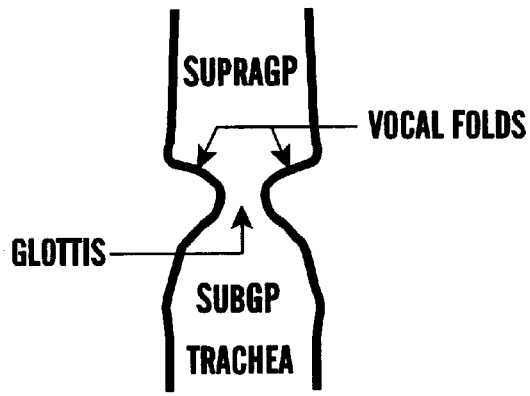
FIG. 1A: Schematic representation of the trachea showing the relationship among subglottal pressure (subGP), supraglottal pressure (supraGP) and transglottal pressure (transGP).
Figure 1B:
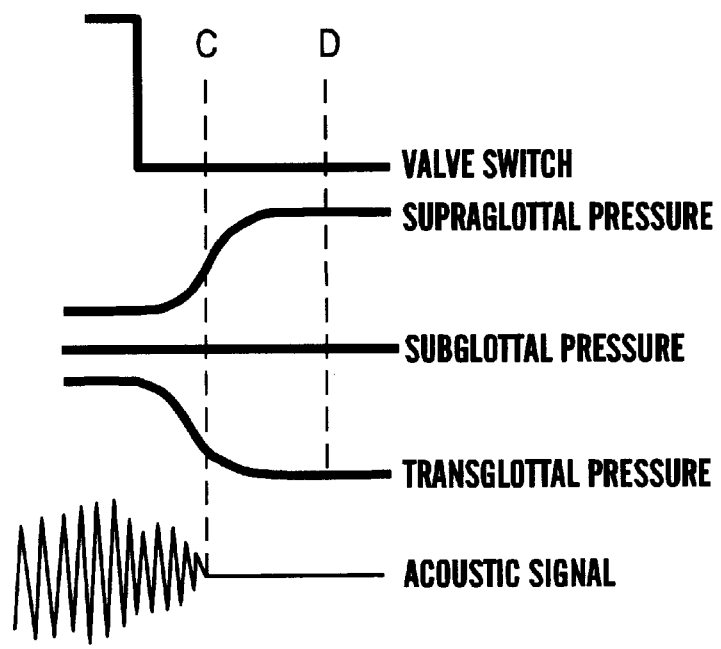
FIG. 1B: Graphic representation of the relationship among supraglottal pressure, s glottal pressure, transglottal pressure and the acoustic signal during airflow interruption (by closure of a valve). C is the time of cessation of phonation, and D is the time when the pressures in the vocal tract equilibrate.

When phonation is interrupted, the supraglottal pressure, or intra-oral pressure, which can be measured non-invasively, rises rapidly to equal the subglottal pressure. However, phonation always ceases before pressure throughout the vocal tract equilibrates. The supraglottal pressure at the point that phonation stops, before the supraglottal pressure has risen to equal the subglottal pressure, is equal to the driving pressure component of the subglottal pressure. Therefore, the difference between the supraglottal pressure at cessation of phonation and the stable supraglottal pressure (which is equal to the subglottal pressure) is the phonation threshold pressure. FIG. 1B shows graphically the relationship among these factors. Referring to FIG. 1B, the phonation threshold pressure may be calculated by measuring the supraglottal pressure at cessation of phonation (C) and at equilibrium (D) and subtracting the supraglottal pressure at C from the supraglottal pressure at D.

The invention provides a device for measuring phonation threshold non-invasively in a human by the airflow interruption technique. The device comprises a housing having a first opening and a second opening. The housing may be any shape, provided the volume of the housing is between about 1–10 cubic inches, preferably between about 1–3 cubic inches. Preferably, the housing is a tube (the tube is, of course, hollow). The tube may have any cross-sectional shape, such as square, rectangular, ellipsoid or circular, but is preferably circular. The housing may be made of any material which is airtight and rigid enough to support the equipment used for making the measurements for determination of phonation threshold pressures, such as rigid plastics, metal or thick cardboard (the cardboard is preferably coated with an air-impervious sealant, such as wax). The housing may be unitary or may be provided in sections which can be connected to form the housing. The connection (s) may be made by any known means, such as friction fit, screwing, clamping, glueing, soldering, etc. If the housing is provided in sections, each section may contain a different component of the device, such as the valve, the microphone, etc., allowing the components to be readily changed to, e.g., replace a malfunctioning component, upgrade a component, to change the arrangement of the components in the housing, etc. If the housing is provided in sections, each section must, of course, contain openings which allow air to flow through the assembled housing.

The device further comprises a member adapted for receiving an airflow from a human's mouth or from a human's mouth and nose and for conveying the airflow into the first opening of the housing. The member comprises a connector adapted for connecting the member to the first opening of the housing. The connection may be permanent or temporary, but is preferably temporary to allow for the use of disposable members. The connection may be made by any known means, such as friction fit, screwing, clamping, glueing, soldering, etc.

The member may be a mask of a size and configuration so that it covers the nose and mouth of the human and forms airtight contact with the human's face. The mask is preferably made of a flexible material in order to conform to the contours of the human face to provide the airtight contact. For instance, the mask can be made of soft rubber, soft plastic, air-filled plastic or gel-filled plastic. Alternatively, the mask could be made of a rigid material having the edges of the mask that contact the human's face coated with a flexible material (e.g., soft rubber, soft plastic, foam, air-filled plastic, or gel-filled plastic glued or otherwise attached to the edges of a mask) for conforming to the contours of the face. The mask must have an opening in it to communicate with the connector so as to convey the airflow from the human's mouth and nose into the housing. Preferably, this opening is approximately in front of the mouth of the human. The mask should also be as small as possible so that as much as possible of the airflow from the human will be directed into the housing and not remain in the mask. Suitable masks are disposable anasthesia masks available commercially from many sources, including Puritan-Bennett, Lenexa, Kans.

The member may also be a mouthpiece for insertion into the mouth of the human. The mouthpiece will comprise a passage that communicates with the connector so as to convey the airflow from the human's mouth into the housing. For instance, the mouthpiece can simply be a piece of round plastic (e.g., polyvinylchloride) tubing having a diameter that fits into a human's mouth. In this case, the other end of the tubing can be used as the connector for connecting the mouthpiece to the first opening of the housing. Alternatively, the mouthpiece can be made of a material (e.g., plastic or soft rubber) which can be shaped to have a configuration conforming to the inside of the mouth, lips, and/or teeth with a hole in it for communication with the connector. If the member is a mouthpiece, the human's nose must be closed during the determination of the phonation threshold pressure with, e.g., nose plugs or a nose clip. Also, it is essential that an airtight seal be maintained between the lips of the human and the mouthpiece.

A valve is positioned with respect to the first and second openings of the housing so that the valve can completely obstruct airflow through the housing when it is in the closed position. For instance, the valve can be positioned in the housing between the first and second openings. The valve may also be connected to the second opening of the housing so that, when the valve is closed, it completely prevents air from flowing out of the second opening. When the valve is connected to the second opening of the housing, it may be inside the housing or outside the housing as long as it prevents air from flowing out of the second opening when it is in the closed position.

The valve is connected to a valve controller, and the valve controller is connected to a valve switch. The valve controller opens and closes the valve in response to a signal from the valve switch. The valve must be capable of being rapidly closed by the valve controller (within about 100 milliseconds) upon actuation of the valve controller by a signal from the valve switch.

Many suitable valves and valve controllers are known and available. A preferred valve is a balloon valve which can be rapidly inflated and deflated with compressed air or other gas by a valve controller. Suitable balloon valves and controllers are available commercially from, e.g., Hans Rudolf, Kansas City, Mo. Another suitable valve is a shutter valve which can be opened and closed by a motor. See Sawashima et al., *Ann. Bull. RILP,* 17,23–32 (1983).

The valve switch may be any simple electrical on/off switch. It is configured so that it simultaneously sends a signal to the valve controller to open or close the valve and a signal to the data acquisition and processing unit which indicates that the valve has been opened or closed.

The device comprises two or three sensors. These sensors are a microphone, a pressure sensor and, preferably, also an airflow sensor. "Sensor" is defined herein to be a device which senses a physical stimulus (e.g., sound, pressure, difference in pressure, airflow) and generates an electrical signal in response to the physical stimulus. "Generate" is used herein to mean that the physical stimulus is converted by the device into an electrical signal and the electrical signal is transmitted to another device. For instance, the electrical signal can be transmitted to a monitor for display. Preferably, however, the electrical signal is amplified so that it can be digitized and analyzed by a computer.

The sensors must be calibrated using physical stimuli of known magnitudes. This calibration should be performed periodically to ensure accurate measurements and must be performed if the size or shape of the housing is varied or if any of the components of the device are changed (e.g., replacing one microphone with another or changing the arrangement of the components of the device).

A microphone is positioned in the housing so as to be able to detect the level (intensity) of the sound made by the human. The location of the microphone in the housing is not critical. Preferably, however, it is located as close as possible to the first opening and, therefore, to the human subject being tested. Locating the microphone in this position avoids even the slight time delay that would result from locating the microphone farther from the first opening, making for more accurate determinations of the cessation of phonation, since the measurements for each test will be made over a period of time that will generally be less than one second. The microphone could also potentially be located in the mask, but this is is generally not practical since the mask must be disinfected or changed between each use. The microphone should be a condensing microphone, not a dynamic microphone. The microphone is connected to an amplifier which amplifies the electrical signal generated by the microphone in response to the level of sound detected by the microphone in the housing.

A pressure sensor is connected to the housing so as to be able to detect the pressure between the first opening of the housing and the valve. The pressure sensor must be accurate, stable and capable of measuring pressures ranging from −20 to +120 cm $H_2O$. The pressure sensor will comprise at least one air collection port. This port can be inserted into the housing between the first opening of the housing and the valve, with the sensor being attached to the outside of the housing. Alternatively, the air collection port on the sensor can be connected to another air collection port positioned in the housing between the first opening of the housing and the valve, with the two ports being connected by an element (e.g., tubing, such as polyethylene tubing) comprising a passage for conveying air from the air collection port located in the housing to the air collection port of the pressure sensor. In another embodiment, if the pressure sensor is sufficiently small, the entire sensor can be positioned in the housing between the first opening of the housing and the valve. The pressure sensor can be a differential pressure sensor, in which case it will have two air collection ports, one of which is used to collect air from the housing, and one of which is used to collect air from the atmosphere or other reference source. The air collection ports of the pressure sensor can be holes or short tubes made of, e.g., glass, plastic, or metal. The air collection ports positioned in the housing may be catheters or short tubes made of, e.g., glass, plastic, or metal. The pressure sensor generates an electrical signal in response to the pressure(s) of the air collected by its air collection port(s) and transmits this electrical signal to another device. Preferably the electrical signal is transmitted to an amplifier (the "pressure signal amplifier") which amplifies the signal so that it can be digitized and analyzed by a computer.

The device of the invention also preferably comprises an airflow sensor connected to the housing so as to be able to detect the level of airflow from the first opening to the second opening of the housing. The airflow sensor is not necessary since airflow measurements are not required for calculating phonation threshold pressure. However, detection of the level of airflow provides confirmation that the device is working properly (e.g., that the valve is closing rapidly and completely) and that the human is performing the test properly. The location of the airflow sensor in the housing is not critical. The airflow sensor may be a differential pressure sensor. This pressure sensor must be accurate, stable and capable of measuring pressures changes of $\pm 2.5$ cm $H_2O$. The differential pressure sensor will comprises two air collection ports. These ports can be inserted into the housing on either side of, and equidistant from, an airflow restrictor. Alternatively, the air collection ports on the sensor can be connected to corresponding air collection ports positioned in the housing on either side of, and equidistant from, an airflow restrictor, with each pair of ports being connected by an element (e.g., tubing, such as polyethylene tubing) comprising a passage for conveying air from the air collection port located in the housing to the air collection port of the sensor. In another embodiment, if the sensor is sufficiently small, the entire sensor can be positioned in the housing, with the airflow restrictor attached to the sensor. The airflow restrictor is any device which can be mounted in the housing to provide resistance to airflow through the housing. For instance, the airflow restrictor may be a wire mesh screen or a semipermeable membrane. The air collection ports of the sensor can be holes or short tubes made of, e.g., glass, plastic, or metal. The air collection ports positioned in the housing may be catheters or short tubes made of, e.g., glass, plastic, or metal. The sensor generates an electrical signal in response to the difference between the pressures of the air collected by its air collection ports (pressure difference=resistance×airflow) and transmits this electrical signal to another device. Preferably the electrical signal is transmitted to an amplifier (the "airflow signal amplifier") which amplifies the signal so that it can be digitized and analyzed by a computer.

The valve switch, the acoustic signal amplifier, the pressure signal amplifier and, where used, the airflow signal amplifer are connected to a data acquisition and processing unit. This unit receives the signals and processes them to provide at least the sound levels and pressures necessary for the calculation of the phonation threshold pressure. Preferably, the data acquisition and processing unit comprises a data acquisition board in a computer loaded with software for digitizing the signals received from the valve switch and the amplifiers and then processing the digitized signals. The computer will provide at least the sound levels and pressures necessary for the calculation of the phonation threshold pressure. This can be provided graphically (see, e.g., FIGS. 3A–B), as a printout in tabular or columnar form, or otherwise. The computer may also be programmed to calculate the phonation threshold pressure directly from the signals.

To determine the phonation threshold pressure of a human, the human is attached to the member of the device and then instructed to make and sustain a phonation at one or more selected acoustic levels, thereby producing an airflow which is conveyed by the member into the housing of the device. Then, the valve switch is switched so as to cause the valve controller to close the valve of the device, thereby obstructing the airflow through the housing. Signals from the valve switch and the amplifiers of the device are collected for a period of time including at least the period beginning with the switching of the valve switch and ending when the pressure in the housing reaches a maximum (generally less than a second). The signals are received and processed by the data acquisition and processing unit of the device, and the phonation threshold pressure is calculated. After a brief period of time (generally 1–3 seconds), the valve switch is switched again to reopen the valve. This process is preferably repeated at least three times at each selected acoustic level, with the interruption of airflow being performed in an irregular (unpredictable) pattern. The multiple phonation threshold pressures are then averaged to give a mean phonation threshold pressure for that human at each of the selected acoustic levels.

It has been found that the phonation threshold pressure is significantly higher in patients suffering from vocal fold polyps and Parkinson's Disease. It is expected that the phonation threshold pressure will also be significantly elevated in other voice disorders and pathologies that affect the vocal tract.

Accordingly, the invention also comprises a method of diagnosing or evaluating a voice disorder or a pathology affecting the vocal tract in a human patient, including evaluating the effectiveness of treatments of such disorders and pathologies. The method comprises determining the phonation threshold pressure of the patient using a device that obstructs an airflow produced by the patient during sustained phonation and comparing the phonation threshold pressure of the patient with the phonation threshold pressures of humans not suffering from a voice disorder or a pathology affecting the vocal tract ("normal controls"), the phonation threshold pressures being determined in the same manner as for the patient. The comparison of the phonation threshold pressures can be made using standard statistical analysis or by comparison of the phonation threshold pressure of the patient with a range of phonation threshold pressures of previously tested normal controls. Preferably, a device like those described herein is used to determine the phonation threshold pressure. Alternatively, other devices known in the art for determining subglottal pressure by airflow interruption can be used. See, e.g., Bard et al., *Ann. Otol. Rhinol. Laryngol.*, 101, 578—582 (1992) and Swashina et al., *Ann. Bull. RILP*, 17, 23–32 (1983).

EXAMPLES

Example 1

Figure 2:
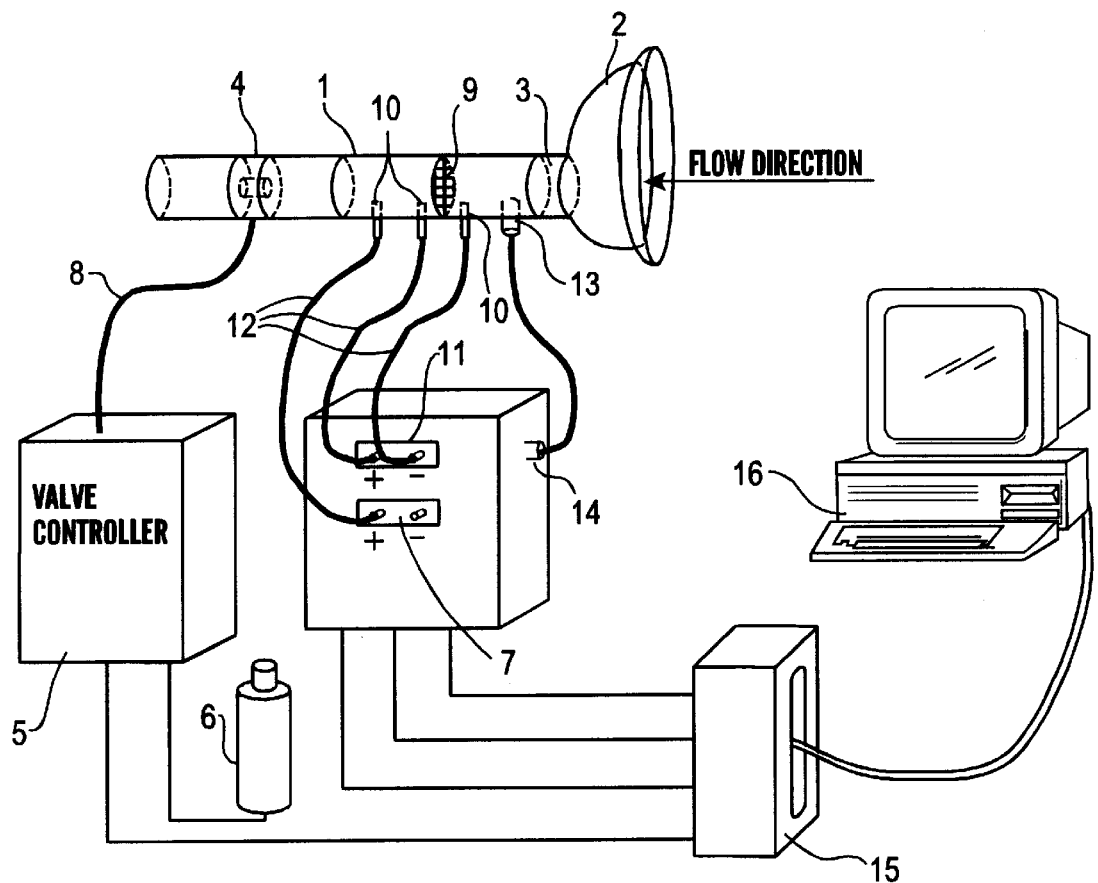
FIG. 2: Schematic diagram of a device according to the invention for measuring phonation threshold pressure by airflow interruption.

Construction of a Device for Measuring PTP Non-invasively by Airflow Interruption A device for measuring phonation threshold pressure (PTP) by the airflow interruption technique was constructed. The device is illustrated schematically in FIG. 2. The device comprised the following components.

Figure 4:
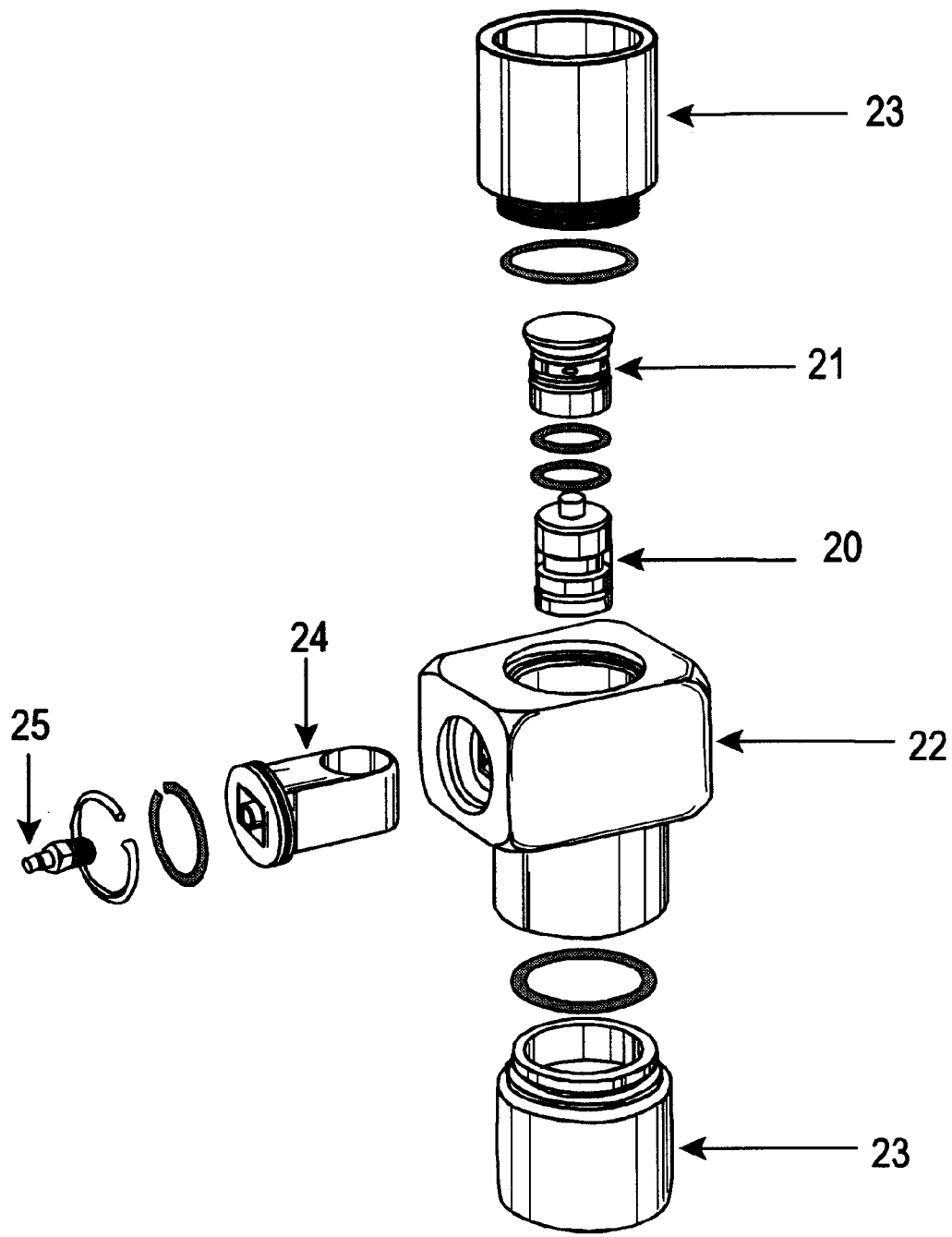
FIG. 4: An exploded view of a Hans Rudolf series 9340 large inflatable balloon-type valve assembly (reproduced from Hans Rudolf Data Sheets).

A large inflatable balloon-type valve assembly 4 (Hans Rudolf, Kansas City, Mo, series 9340 two-way shutoff large inflatable balloon-type valve) was placed in a plastic pipe 1 of ⅞" outside diameter. An exploded view of the valve assembly is presented in FIG. 4. The valve assembly comprises a replaceable balloon assembly 20. The balloon assembly consists of a molded silicone rubber balloon mounted on a white plastic mandrel. The balloon assembly is attached to a center piece 21 and mounted in a pneumatic housing 24 inside a larger housing 22 to which are attached two inlet/outlet ports 23. When the balloon is deflated, air can flow in either direction through the inlet/outlet ports. When the balloon is inflated, flow in both directions is shut off. The outside diameter (0.875") of the inlet/outlet ports was selected to provide an airtight friction fit when inserted into the plastic pipe (inner diameter of 0.875"). In the device, only one of the inlet/outlet ports was inserted into the end of the plastic pipe opposite that end to which the mask was attached (see FIG. 2). If desired, the second inlet/outlet port could be inserted into a second piece of plastic pipe for mounting some of the other components of the device. In particular, the microphone and/or the components used for measuring airflow could be located in this second piece of pipe. The components used for measuring pressure must, of course, be located between the mask and the valve.

The valve could be closed rapidly (within 84 ms) by a valve controller 5 (Hans Rudolf series 9330 automated controller) to completely block airflow through the pipe. A double piston pump assembly is the device in the controller that inflates/deflates the balloon with air from a compressed air supply (50–90 psi). The gas used for inflation can also be oxygen or helium. The controller is connected to the compressed air by means of pneumatic tubing. The controller is also connected to the valve assembly by means of pneumatic tubing 8 (see FIG. 2). The pneumatic tubing is connected to a connector 25 on the pneumatic housing 24 of the valve assembly (see FIG. 4). The tubing 8 connecting the controller to the valve assembly should be no more than 4–10 feet in length. When the pump is actuated, it displaces a volume of air to the balloon assembly. When the pump is deactuated, it deflates the balloon assembly by pulling air from it. The valve controller is actuated/deactuated by a manual on/off switch 6.

For a more detailed description of this system, see the Hans Rudolph Data Sheets, the complete disclosures of which are incorporated herein by reference.

A form fitting disposable anesthesia type mask 2 (Puritan-Bennett, Lenexa, Kans., model 133264-00 with ⅞" inside diameter fitting 3) was attached to the pipe by friction fit (outside diameter of the plastic pipe was ⅞").

A microphone 13 (Sony, San Jose, Calif., Model PDM201D ECM-T150 microphone) was mounted in the plastic pipe so that it would be 2.75" from the lips of the test subject. The microphone was mounted by gluing it to the pipe and sealing the hole in the pipe through which it passes with silicone. The microphone was connected to an amplifier 14. The microphone was calibrated at known intensities with a Quest Electronics, Oconomowoc, Wisc, Model 2800 impulse integrating sound level meter.

To measure airflow, a mesh wire screen 9 spanning a cross-sectional area of the pipe was friction fit and glued to the inside of the pipe. Two plastic ports 10, one on either side of the screen, each equidistant from the screen, were glued to the pipe, and the holes through which they passed sealed with silicone. The closest port of the two was located 1.25" from the microphone. The ports 10 were connected by flexible polyethylene tubing 12 to the ports in an airflow sensor/amplifier 11 (Honeywell, Freeport, Ill., Micro Switch Model 163PC01D75 amplified low pressure differential sensor; able to detect pressure changes of±2.5 cm $H_2O$). When air flows through the pipe, there is a difference in pressure on the two sides of the screen, and the pressure difference is directly related to the airflow through the pipe (difference in pressure=resistance×airflow). The airflow sensor/amplifier converts the difference in pressure at the two ports into an electrical signal (volts) representative of the airflow and then amplifes this signal. The airflow sensor was calibrated at known airflows using a Gilmont, Barrington, Ill., model F-2060 size 14 shielded flow meter. A second order equation (flow=(12.43938×volts)−(1.074513×volts$^2$)) was found to describe the relationship between the airflow and the output voltage.

To measure pressure, another port 10, identical to those used to measure airflow, was glued in the pipe 1.00" from the closest airflow measuring port, and the hole through which the port passed was sealed with silicone. The port was connected by polyethylene tubing 12 to a port on a pressure sensor/amplifier 7 (Honeywell Micro Switch Model 163PC01D48 amplified low pressure differential sensor; pressure range −20 to +120 cm $H_2O$). The second port of the sensor/amplifier was left open to the atmosphere. The difference between the pressure in the pipe and the atmospheric pressure (set to be zero relative to the pressure in the pipe) was the signal output (in volts). This signal was amplified by the amplifer of the sensor/amplifer. The pressure sensor was calibrated using a Sen-Sym, Milpitas, Calif., digital manometer that provides accurate known pressures. A linear relationship (pressure=(3.022998×volts) was found to describe the pressure calibration.

The outputs of the three amplifiers and a signal from the valve inflate/deflate switch were relayed by BNC (bayonet nut connector) cable to a data acquisition board 15 (National Instruments, Austin, Tex., Model AT-MIO-16 series) and digitized (using custom programmed Voice Analyzer data acquisition software written using National Instruments Labview graphical programming language). Suitable software is also available commercially. The digitized signals were processed using a standard personal computer 16 running Windows 95, and the data were output in the form of graphs (see FIGS. 3A–B). Using the graphs, the phonation threshold pressures were calculated. This calculation could also be performed by the computer automatically if provided with suitable additional software.

Example 2

Evaluation of the Device in a Subject with a Normal Larynx and Direct Access to the Subglottis The device of Example 1 was tested with a human subject. The subject had a normal larynx, but had a tracheostomy placed for nocturnal sleep apnea.

The mask was placed comfortably over the mouth and nose of the subject and held in airtight contact with the subject's face by the subject or the technician performing the test. The subject was asked to sustain 3 different /a/ tones: soft (75 dB), medium (80 dB), and loud (85 dB). During the sustained phonations, the valve controller was used to cause brief (500 ms) closures (inflation) of the valve, interrupting airflow in an unpredictable pattern.

The actual subglottal pressure was obtained by placing a pressure sensor into the subglottic trachea of the patient through the tracheostomy tube and sealing around the transducer wire as well as the tracheostomy tube.

In multiple tests of this subject, the subglottic pressures measured using the device of Example 1 and the actual subglottic pressures measured through the tracheostomy tube demonstrated good agreement. A linear regression (equation: airflow interruption pressure=0.5778+0.9271× actual tracheostomy pressure) resulted in a $r^2$ correlation factor of 0.9550 between the pressures measured by airflow interruption and the pressures measured through the tracheostomy tube.

Figure 3A:
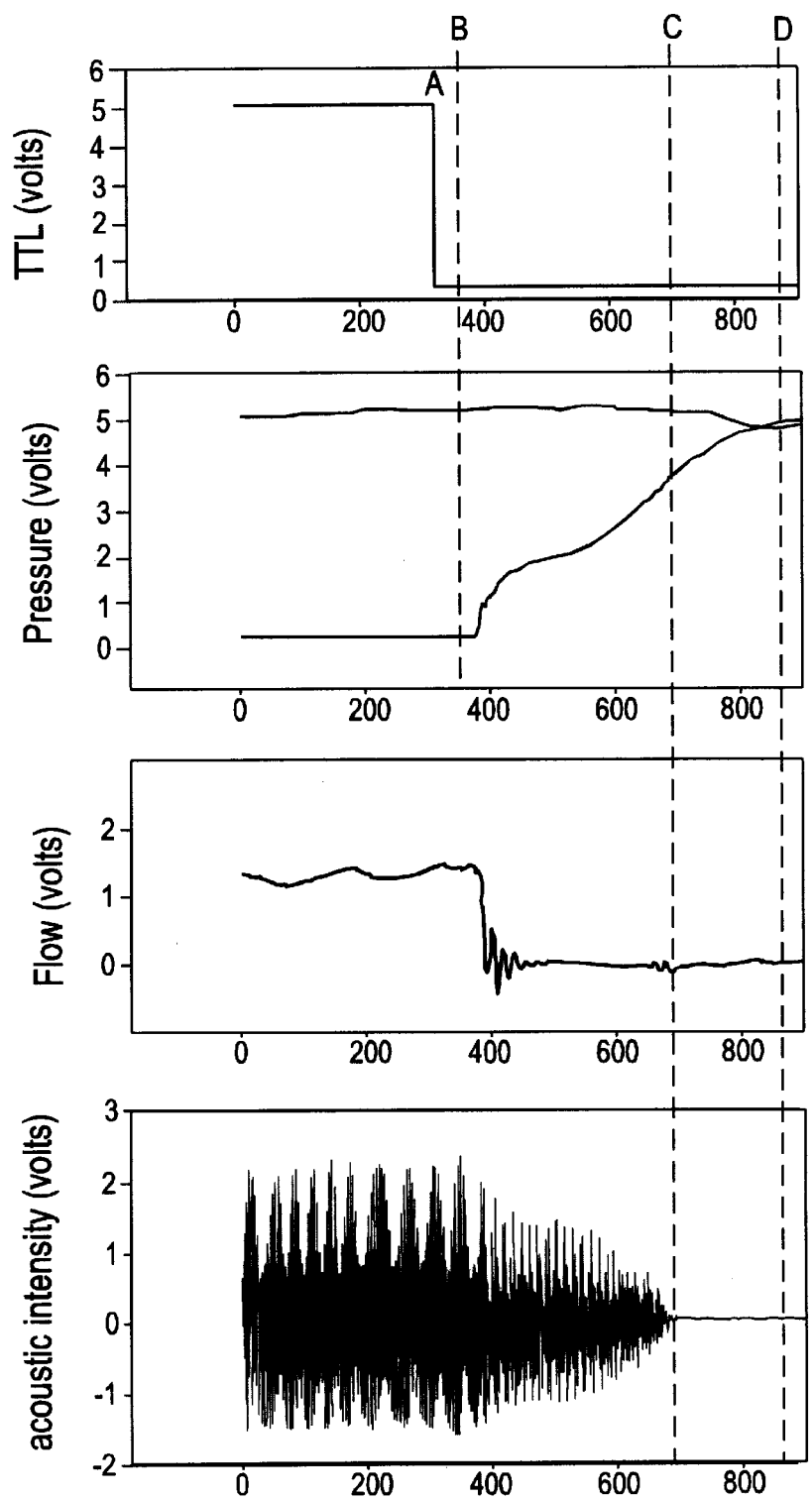
FIGS. 3A–B: Graphs of TTL (transistor-transistor logic; a family of digital electronic signals), supraglottal pressure, airflow, and acoustic level versus time measured using the device depicted in FIG. 2 in a typical trial for a patient with a normal larynx, but having a tracheostomy tube in place (FIG. 3A) and for a patient with vocal fold polyps (FIG. 3B). Point A is the time at which the valve was closed causing obstruction and interruption of the airflow. Point B is the time at which the pressure above the glottis (supraglottal pressure) started to rise and the intensity of phonation and the airflow decreased. Point C is the time at which acoustic signal of phonation ceased, after which the pressure continued to rise until it stabilized at a flat level (point D).

FIG. 3A shows measurements made using the device of Example 1 during a typical trial in this patient. At point A, the valve closes (inflates). At point B, pressure above the glottis (supraglottal pressure) starts to rise and the intensity of phonation and the airflow decrease. At point C, the acoustic signal of phonation stops, but supraglottal pressure continues to rise until it stabilizes at a flat level, point D. The difference in pressure between point C, when phonation ceases, and point D, flat pressure signal, is the phonation threshold pressure. In FIG. 3A, the actual subglottal pressure measured through the tracheostomy tube is also shown.

Example 3
Use of the Device to Evaluate PTPs in Normal Subjects and Patients with Vocal Fold Polyps Normal subjects and patients with vocal fold polyps were tested with the device of Example 1 using the protocol described in Example 2. None of the subjects or patients had tracheostomy tubes, so direct pressures were not measured. If the patients with polyps were unable to produce phonation at the requested intensity levels, the targets for soft, medium, and loud were reduced by 10 dB. The phonation threshold pressure at each of these levels was calculated. The subjects could not anticipate the brief interruptions of phonation, and the obstruction of the airflow was released before there were any measurable adjustments in respiratory force.

The mean phonation threshold pressures of normal human subjects were 2.38, 2.67, and 2.98 cm $H_2O$ at 75, 80, and 85 dB, respectively. The mean phonation threshold pressures of the subjects afflicted with vocal polyps were 3.73, 4.20, 4.79, 5.85, and 7.37 cm $H_2O$ at 65, 70, 75, 80, and 85 dB, respectively. Table 1 summarizes these results and shows the standard deviations. The differences in mean phonation threshold pressures between groups at 75, 80, and 85 dB were significant at p=0.013, p=0.017, and p=0.010, respectively. The ratio of normal subject's mean phonation threshold pressures to abnormal patient's mean phonation threshold pressures at each phonation level was 2.2 times greater for patients with vocal polyps.

Figure 3B:
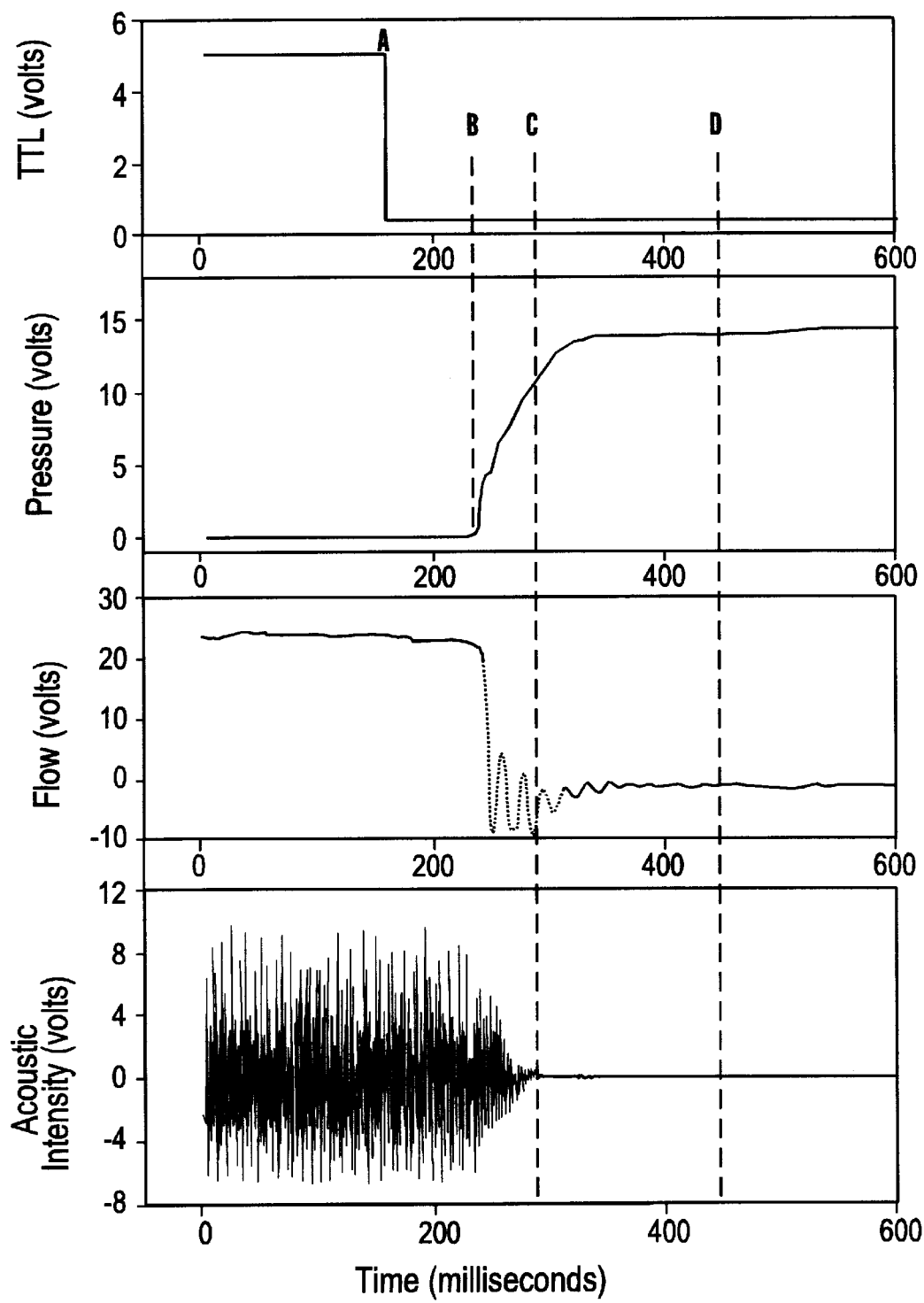

FIG. 3B shows measurements made using the device of Example 1 during a typical trial of a patient with vocal fold polyps. At point A, the valve closes (inflates). At point B, pressure above the glottis (supraglottal pressure) starts to rise and the intensity of phonation and the airflow decrease. At point C, the acoustic signal of phonation stops, but supraglottal pressure continues to rise until it stabilizes at a flat level, point D. The difference in pressure between point C, when phonation ceases, and point D, flat pressure signal, is the phonation threshold pressure.

Measures of phonation threshold pressure during voice production of normal subjects ranged from less than 1 cm of water pressure to over 7 centimeters of water pressure. The data demonstrate that there is quite a range of phonation threshold pressure among voices that are perceived as normal.

Only three patients of the 13 with polyps on their vocal folds could produce phonation at 80 and 85 dB. There was a range of phonation pressures measured in patients with vocal polyps which was greater than that seen in the normal subjects. During the vocal productions of the patients with vocal polyps, measured phonation threshold pressures were significantly higher than for the normal patients.

The phonation threshold pressures obtained in this study fall into the accepted range of 1 to 10 cm $H_2O$ (Titze, in *Vocal physiology: voice production, mechanisms and functions*, pages 227–238 (Fugimura ed., Raven Press, 1988)). Although the values generally concur with other studies, it is not surprising they do not match precisely. This device stops the airflow, resulting in loss of phonation and measures the pressure at the point that phonation is no longer sustained. Other studies have measured the pressure generated at the onset of phonation rather than cessation of voiced sound. Separate glottal configurations presumably exist for the different instants of measurement. These unique glottal configurations may lead to variance in aerodynamic measurement values.

Experience with these studies has shown that subjects sometimes relax, close the glottis, and stop phonating on their own, which does not provide the information necessary to calculate phonation threshold pressure. Also, even when airflow is cut off, the vocal tract can still generate sound. The microphone does not detect the difference between a genuine phonation and continuation of some noise after airflow is cut off. Without a distinct cessation of phonation, the phonation threshold pressure cannot be calculated with this method. Other factors that appear to be important are the fit of the mask and its position. If the seal of the mask is not airtight, air leaks out and the pressure measured is not an accurate measurement. Steps must be taken to check for and avoid these variables to ensure that accurate measurements and phonation threshold pressures are obtained.

TABLE 1

|  | PTP (SD) | | |
| --- | --- | --- | --- |
|  | 75 dB | 80 dB | 85 dB |
| Normal Subjects (n = 11) | 2.379 (1.273) | 2.671 (1.879) | 2.985 (2.225) |

|  | PTP (SD) | | | | |
| --- | --- | --- | --- | --- | --- |
|  | 65 dB | 70 dB | 75 dB | 80 dB | 85 dB |
| Polyp Patients (n = 13) | 3.734 (2.194) | 4.198 (2.50l) | 4.792 (2.672) | 5.851 (2.342) | 7.374 (3.255) |

PTP = phonation threshold pressure; SD = standard deviation; dB = decibles.

Example 4
Determining the PTP of Normal Controls and Patients with Parkinson's Disease Parkinson's Disease is a neuromuscular disease resulting from a deficiency of nigrostriatal dopamine. The movement disorder that results affects muscle groups in the body, including the muscular groups used in speech production. Common voice peculiarities characteristic of patients with Parkinson's Disease involve reduced volume, narrowed range of both pitch and volume, imprecise articulation, disordered rate, hoarseness, breathiness, and a tremulous voice. Overall, the speech defects in Parkinson's Disease patients appear to be the consequences of reduced respiratory support and insufficient glottal closure caused by the rigidity and weakness of the laryngeal and respiratory muscle groups.

Subjects were tested as described in Example 2 using the device of Example 1. None of the subjects had tracheostomy tubes, so direct pressures were not measured. The subjects consisted of two groups: (1) the patients with Parkinson's Disease (n=19); and (2) the normal subjects (n=11). Neurologists examined and referred the patients with Parkinson's Disease. The Hoehn and Yahn ratings determined the idiopathic etiology of the disease, from stage 1 to 3 (Hoehn and Yahn, *Neurology* 17:427–42 (1967)). They were from 45 to 80 years of age and possessed adequate cognitive speech intelligibility as judged by the clinician.

The mean phonation threshold pressures of the normal human subjects were 2.38 cm $H_2O$ at 75 dB, 2.67 cm $H_2O$ at 80 dB, and 2.98 cm $H_2O$ at 85 dB. The mean phonation threshold pressures of the patients with Parkinson's Disease were 1.11 cm $H_2O$ at 65 dB, 2.84 cm $H_2O$ at 70 dB, 4.14 cm $H_2O$ at 75 dB, 5.46 cm $H_2O$ at 80 dB, and 7.46 cm $H_2O$ at 85 dB. Table 2 summarizes these results and shows the standard deviations. The differences in mean phonation threshold pressures of the normal subjects and Parkinsons' patients at 75, 80 and 85 dB were significant at the p=0.039, p=0.017, and p=0.015 levels, respectively. The phonation threshold pressure of the patients with Parkinson's Disease was on average 2.1 times greater than the phonation threshold pressure of the normal subjects (the ratio of abnormal patient's mean phonation threshold pressures to normal subject's mean phonation threshold pressures at each phonation level).

A significantly increased phonation threshold pressure at three different intensity levels was observed for the Parkinson's Disease patients when compared to control subjects. It is hypothesized that the increased phonation threshold pressure is related to greater stiffness and change in configuration of the glottal aperture. These data are consistent with observations of Ramig et al. (Ramig, et al., *J. Sp. Hear. Res.* 38:1232–1251 (1995)) that patients with Parkinson's Disease feel that they are actually using a great deal more effort to produce a phonation of particular intensity than the measured acoustic intensity indicates. These data indicate that patients with Parkinson's disease do indeed require greater subglottal force to sustain phonation than normal speakers do.

TABLE 2

|  | PTP (SD) | | |
| --- | --- | --- | --- |
|  | 75 dB | 80 dB | 85 dB |
| Normal Subjects (n = 11) | 2.379 (1.273) | 2.671 (1.879) | 2.985 (2.225) |

|  | PTP (SD) | | | | |
| --- | --- | --- | --- | --- | --- |
|  | 65 dB | 70 dB | 75 dB | 80 dB | 85 dB |
| Park. Patients (n = 1.9) | 1.107 (0.579) | 2.836 (2.154) | 4.138 (2.499) | 5.463 (3.178) | 7.456 (4.928) |

We claim:

1. A device for measuring a phonation threshold pressure in a human comprising:

a housing having a first opening and a second opening;

a member adapted for receiving an airflow from a human's mouth or from a human's mouth and nose and for conveying the airflow into the first opening of the housing, the member comprising a connector adapted for connecting the member to the first opening of the housing;

a valve having at least an open and a closed position, the valve being positioned with respect to the first and second openings of the housing so that the valve can completely obstruct air flow through the housing when it is in the closed position, the valve being connected to a valve controller, the valve controller being connected to a valve switch which can generate an electrical signal, the valve controller being adapted to open and close the valve in response to the signal from the valve switch;

a microphone positioned in the housing so as to detect the level of sound in the housing, the microphone being capable of generating an electrical signal in response to the level of sound detected by the microphone, the microphone being connected to an acoustic signal amplifier which amplifies the electrical signal generated by the microphone; and a pressure sensor connected to the housing so as to be able to detect the level of pressure between the first opening of the housing and the valve, the pressure sensor being capable of generating an electrical signal in response to the level of pressure detected by the pressure sensor, the pressure sensor being connected to a pressure signal amplifier which amplifies the electrical signal generated by the pressure sensor;

the valve switch, acoustic signal amplifier, and pressure signal amplifier being connected to a data acquisition and processing unit that receives and processes the signals from the valve switch and the two amplifers to provide at least the sound levels and pressures necessary for the calculation of the phonation threshold pressure.

2. The device of claim 1 further comprising an airflow sensor connected to the housing so as to be able to detect the level of airflow from the first opening to the second opening of the housing and being capable of generating an electrical signal in response to the level of the airflow detected by the airflow sensor, the airflow sensor being connected to an airflow signal amplifier which amplifies the electrical signal generated by the airflow sensor, the airflow signal amplifier being connected to the data acquisition and processing unit which receives and processes the signal from the amplifier.

3. The device of claim 1 wherein the member is a mask of a size and configuration so that it covers the nose and mouth of the human and forms airtight contact with the human's face, the mask comprising an opening that communicates with the connector so as to convey the airflow from the human's mouth and nose into the housing.

4. The device of claim 1 wherein the member further comprises a mouthpiece adapted for insertion into the mouth of the human, the mouthpiece comprising a passage that communicates with the connector so as to convey the airflow from the human's mouth into the housing.

5. The device of claim 1 wherein the data acquisition and processing unit comprises a data acquisition board in a computer loaded with software for digitizing the signals received from the valve switch and the amplifiers.

6. A device for measuring a phonation threshold pressure in a human comprising:

a tube having a first end and a second end;

a member adapted for receiving an airflow from a human's mouth or from a human's mouth and nose and for conveying the airflow into first end of the tube, the member comprising a connector adapted for connecting the member to the first end of the tube;

a valve having at least an open and a closed position, the valve being positioned with respect to the first and second ends of the tube so that the valve can completely obstruct air flow through the tube when it is in the closed position, the valve being connected to a valve controller, the valve controller being connected to a valve switch which can generate an electrical signal, the valve controller being adapted to open and close the valve in response to the signal from the valve switch;

a microphone positioned in the tube so as to be able to detect the level of sound in the tube, the microphone being capable of generating an electrical signal in response to the level of sound detected by the microphone, the microphone being connected to an acoustic signal amplifier which amplifies the electrical signal generated by the microphone; and a pressure sensor connected to the tube so as to be able to detect the level of pressure between the first end of the tube and the valve, the pressure sensor being capable of generating an electrical signal in response to the level of the pressure detected by the pressure sensor, the pressure sensor being connected to a pressure signal amplifier which amplifies the electrical signal generated by pressure sensor;

the valve switch, acoustic signal amplifier, and pressure signal amplifier being connected to a data acquisition and processing unit that receives and processes the signals from the valve switch and the two amplifiers to provide at least the sound levels and pressures necessary for the calculation of the phonation threshold pressure.

7. The device of claim 6 further comprising an airflow sensor connected to the tube so as to be able to detect the level of airflow from the first end to the second end of the tube and being capable of generating an electrical signal in response to the level of the airflow detected by the airflow sensor, the airflow sensor being connected to an airflow signal amplifier which amplifies the electrical signal generated by the airflow sensor, the airflow signal amplifier also being connected to the data acquisition and processing unit which receives and processes the signal from the amplifier.

8. The device of claim 6 wherein the member is a mask of a size and configuration so that it covers the nose and mouth of the human and forms airtight contact with the human's face, the mask comprising an opening that communicates with the connector so as to convey the airflow from the human's mouth and nose into the first opening of the tube.

9. The device of claim 6 wherein the member further comprises a mouthpiece adapted for insertion into the mouth of the human, the mouthpiece comprising a passage that communicates with the connector so as to convey the airflow from the human's mouth into the first opening of the tube.

10. The device of claim 6 wherein the data acquisition and processing unit comprises a data acquisition board in a computer loaded with software for digitizing the signals received from the valve switch and the amplifiers.

11. The device of claim 6 wherein the microphone is located between the first end of the tube and the valve.

12. A device for measuring a phonation threshold pressure in a human comprising:

a cylindrical tube having a first end and a second end;

a mask of a size and configuration so that it covers the nose and mouth of the human and forms airtight contact with the human's face, the mask comprising an opening communicating with a connector, the connector being adapted for connecting the mask to the first end of the tube so as to convey the airflow from the human's mouth and nose into the tube through the first end of the tube;

a valve having at least an open and a closed position, the valve being positioned with respect to the first and second ends of the tube so that the valve can completely obstruct air flow through the tube when it is in the closed position, the valve being connected to a valve controller, the valve controller being connected to a valve switch which can generate an electrical signal, the valve controller being adapted to open and close the valve in response to the signal from the valve switch;

a microphone positioned in the tube so as to be able to detect the level of sound in the tube, the microphone being capable of generating an electrical signal in response to the level of sound detected by the microphone, the microphone being connected to an acoustic signal amplifier which amplifies the electrical signal generated by microphone; and a pressure sensor connected to the tube so as to be able to detect the pressure between the first end of the tube and the valve, the pressure sensor being capable of generating an electrical signal in response to the level of the pressure detected by the pressure sensor, the pressure sensor being connected to a pressure signal amplifier which amplifies the signal generated by the pressure sensor;

the valve switch, acoustic signal amplifier and pressure signal amplfier being connected to a data acquisition and processing unit that receives and processes the signals from the valve switch and the two amplifiers to provide at least the sound levels and pressures necessary for the calculation of the phonation threshold pressure.

13. The device of claim 12 further comprising an airflow sensor connected to the tube so as to be able to detect the level of airflow from the first end to the second end of the tube and being capable of generating an electrical signal in response to the level of the airflow detected by the airflow sensor, the airflow sensor being connected to an airflow sensor amplifier which amplifies the signal generated by the airflow sensor, the airflow signal amplifier being connected to the data acquisition and processing unit which receives and processes the signal from the amplifier.

14. The device of claim 12 wherein the data acquisition and processing unit comprises a data acquisition board in a computer loaded with software for digitizing the signals received from the valve switch and the amplifiers.

15. The device of claim 12 wherein the microphone is positioned in the tube between the first end of the tube and the valve.

16. The device of claim 12 wherein the valve is positioned in the tube between the first end of the tube and the second end of the tube.

17. The device of claim 12 wherein the valve is connected to the second end of the tube so that the valve completely obstructs air flow through the tube when it is in the closed position.

18. The device of claim 12 wherein the valve is a balloon valve.

19. The device of claim 18 wherein the balloon valve is located in a housing having an inlet port and an outlet port and the inlet port is connected to the second end of the tube so that the valve completely obstructs air flow through the tube when it is in the closed position.

20. The device of claim 12 wherein the pressure sensor comprises at least one air collection port, and the air collection port of the pressure sensor is connected to an air collection port located in the tube between the first end of the tube and the valve, the two ports being connected by an element comprising a passage for conveying air from the air collection port located in the tube to the air collection port of the pressure sensor.

21. The device of claim 20 wherein the microphone is positioned in the tube between the first end of the tube and the valve and the air collection port is located in the tube between the microphone and the valve.

22. The device of claim 13 wherein the airflow sensor comprises two air collection ports, and the air collection ports of the sensor are connected to corresponding air collection ports located in the tube, one of the ports in the tube being located on one side of, and at a selected distance from, an airflow restrictor, the other port in tube being located on the other side of, and an equal distance from, the restrictor, each of the ports in the tube being connected to a corresponding port on the sensor by an element comprising a passage for conveying air from the port located in the tube to the port of the pressure sensor.

23. The device of claim 22 wherein the airflow restrictor is a wire mesh screen.

24. A method of determining a phonation threshold pressure in a human comprising:

having the human make and sustain a phonation at one or more selected acoustic levels, thereby producing an airflow which is conveyed into the housing of the device of claim 1;

switching the valve switch so as to cause the valve controller to close the valve of the device, thereby obstructing the airflow through the housing of the device;

acquiring signals from the valve switch and the amplifiers of the device for a period of time from at least the time of the switching of the valve switch until the pressure in the housing reaches a maximum; and processing the signals to calculate the phonation threshold pressure.

25. A method of determining a phonation threshold pressure in a human comprising:

having the human make and sustain a phonation at one or more selected acoustic levels, thereby producing an airflow which is conveyed into the tube of the device of claim 6;

switching the valve switch so as to cause the valve controller to close the valve of the device, thereby obstructing the airflow through the tube;

acquiring signals from the valve switch and the amplifiers of the device for a period of time from at least the time of the switching of the valve switch until the pressure in the tube reaches a maximum; and processing the signals to calculate the phonation threshold pressure.

26. A method of determining a phonation threshold pressure in a human comprising:

having the human make and sustain a phonation at one or more selected acoustic levels, thereby producing an airflow which is conveyed into the tube of the device of claim 12;

switching the valve switch so as to cause the valve controller to close the valve of the device, thereby obstructing the airflow through the tube;

acquiring signals from the valve switch and the amplifiers of the device for a period of time from at least the time of the switching of the valve switch until the pressure in the tube reaches a maximum; and processing the signals to calculate the phonation threshold pressure.

27. A method of diagnosing or evaluating a voice disorder or a pathology affecting the vocal tract in a human patient comprising:

determining the phonation threshold pressure of the patient using a device that briefly obstructs an airflow produced by the patient during sustained phonation; and comparing the phonation threshold pressure of the patient with the phonation threshold pressures of humans not suffering from a voice disorder or a pathology affecting the vocal tract, the phonation threshold pressures being determined in the same manner as for the patient.

28. The method of claim 27 wherein the voice disorder is caused by vocal fold polyps.

29. The method of claim 27 wherein the pathology affecting the vocal tract is Parkinson's Disease.

* * * * *